US00PP24665P2

(12) United States Plant Patent
Zaiger et al.

(10) Patent No.: US PP24,665 P2
(45) Date of Patent: Jul. 22, 2014

(54) INTERSPECIFIC TREE NAMED 'AUTUMN BLISS'

(50) Latin Name: ***Interspecific Prunus* species**
Varietal Denomination: Autumn Bliss

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 6 days.

(21) Appl. No.: 13/694,930

(22) Filed: Jan. 22, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth habit.
2. The tree being a regular and productive bearer of large size fruit.
3. Fruit with an attractive, dark red skin color.
4. Fruit with an average Brix of 20.8° and a good balance between acid and sugar.
5. Fruit with very good flavor and eating quality.
6. Fruit with good handling and shipping qualities.

1 Drawing Sheet

Botanical designation: Interspecific *Prunus* species.
Variety denomination: 'Autumn Bliss'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of interspecific, which are known to us, and mentioned herein, 'Flavor Fall' Interspecific (U.S. Plant Pat. No. 11,990), 'Fall Fiesta' Interspecific (U.S. Plant Pat. No. 22,428) and our proprietary non-patented interspecific seedlings '146LH291', '328LC181' and '78EG416'.

STATEMENT REGARDING FEDERALLY SPONSORED RESEARCH AND DEVELOPMENT

Not applicable.

ORIGIN OF THE VARIETY

The new and distinct variety of interspecific tree consists of the combination *of Prunus salicina* and *Prunus armeniaca*. It was originated by us in our experimental orchard located near Modesto, Calif. as a first generation cross between our non-patented interspecific seedling '146LH291' and 'Flavor Fall' Interspecific (U.S. Plant Pat. No. 11,990). Our seed parent '146LH291' interspecific seedling selection (non-patented) originated as a first generation cross between our two proprietary non-patented interspecific seedling selections with the field identification numbers '328LC181' and '78EG416'. A large number of these first generation seedlings (146LH291× Flavor Fall) were planted and grown on their own root system and under close and careful observation, one such seedling, which is the present variety, exhibited desirable tree and fruit characteristics and was selected in 2002 for additional asexual propagations and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree is of large size, vigorous, upright growth and a regular and productive bearer of large size, clingstone fruit with very good flavor and eating quality. The fruit is further characterized by having dark red skin, yellow flesh and having good handling and storage quality. In comparison to its seed parent '146LH291' interspecific (non-patented) the fruit of the new variety has a higher degree of attractive dark red skin color and is approximately 41 days later in maturity. In comparison to its pollen parent 'Flavor Fall' Interspecific (U.S. Plant Pat. No. 11,990) the fruit of the new variety is heart shaped compared to globose, has a higher Brix of 20.8° compared to 17.4° and is approximately 10 days later in maturity. In comparison to the commercial interspecific 'Fall Fiesta' (U.S. Plant Pat. No. 22,428) the fruit of the new variety is larger in size and is approximately 26 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 9 year old specimens grown near Modesto, Calif., with color in accordance with Munsell Book of Color published in 1958.

Tree:

*Size*.—Large, usually pruned to 3 to 3.5 meters in height and width for economical harvesting of fruit.

*Vigor*.—Vigorous, growth of 1.5 to 2 meters in height the first growing season. Varies slightly with soil type, fertility and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 7 consecutive years. No alternate bearing observed.

*Fertility*.—Self-sterile, pollinator required.

*Density*.—Medium dense, usually pruned to vase shape to increase air movement and sunlight to center of tree to enhance fruit color and health of fruit spurs.

*Hardiness*.—Hardy in all stone fruit growing areas of California. Tree grown in USDA Hardiness Zone 9. Winter chilling requirement approximately 850 hours at or below 45° F.

Trunk:

*Size*.—Medium. Average circumference 48.3 cm at 25.4 cm above ground on a 9 year old tree.

*Stocky*.—Medium stocky.

*Texture*.—Medium shaggy, increases with age of tree.

*Color*.—Varies from 10YR 4/2 to 5Y 3/2.

Branches:

*Size*.—Medium. Average circumference 16.3 cm at 1.2 meters above ground on a 9 year old tree. Crotch angle approximately 30°, increases with heavy crop load.

*Surface texture*.—New growth relatively smooth. Mature growth medium rough, roughness increases with age.

*Lenticels*.—Average number 24 in a 25.8 sq cm section. Average length 4.6 mm. Average width 2.1 mm. Color varies from 5YR 4/8 to 7.5YR 4/8.

*Color*.—New growth varies from 2.5GY 5/4 to 5GY 5/4. Mature growth varies from 7.5YR 7/2 to 7.5YR 3/2, varies with age of growth.

Leaves:

*Size*.—Small. Average length 69.5 mm. Average width 32.5 mm.

*Form*.—Lanceolate.

*Apex*.—Acuminate.

*Base*.—Cuneate.

*Margin*.—Serrulate.

*Thickness*.—Medium.

*Surface texture*.—Upper surface relatively smooth, slight indentations over midrib and leaf veins. Lower surface relatively smooth, small ridges created by midrib and pinnate venation. Both upper and lower surfaces glabrous.

*Petiole*.—Average length 9.8 mm. Average width 1.0 mm. Longitudinally grooved. Surface — glabrous. Color varies from 2.5GY 6/6 to 5GY 6/6.

*Glands*.—Eglandular.

*Stipules*.—None present at time of measurement.

*Color*.—Upper surface varies from 7.5GY 3/6 to 7.5GY 4/6. Lower surface varies from 5GY 5/4 to 2.5GY 6/4. Midvein color varies from 5GY 7/2 to 2.5GY 6/4.

Flower buds:

*Size*.—Small to medium. Average length 8.7 mm. Average diameter 6.0 mm.

*Hardiness*.—Hardy with respect to California winters.

*Form*.—Conical, becoming elongated just before opening.

*Pedicel*.—Average length 7.6 mm. Average width 0.6 mm. Color varies from 2.5GY 6/6 to 5GY 6/6.

*Color*.—N 9.5/ (white).

*Number of buds per spur*.—Varies from 13 to 22, average number 16.

Flowers:

*Blooming period*.—Date of First Bloom Feb. 21, 2012. Date of Petal Fall Mar. 3, 2012, varies slightly with climatic conditions.

*Size*.—Small to medium. Average height 11.2 mm. Average diameter 17.1 mm.

*Petals*.—Normally 5, alternately arranged to sepals. Size — small to medium. Average length 8.8 mm. Average width 6.7 mm. Form — globose. Margin — sinuate. Both upper and lower surfaces glabrous. Color N 9.5/ (white).

*Sepals*.—Normally 5, alternately arranged to petals. Size — small. Average length 2.4 mm. Average width 2.3 mm. Shape — triangular. Margin — entire. Both upper and lower surfaces glabrous. Color — upper surface varies from 5GY 5/6 to 5GY 5/8. Lower surface varies from 5GY 5/8 to 5GY 5/6.

*Stamens*.—Average number per flower 27. Average filament length 6.9 mm. Filament color N 9.5/ (white). Anther color varies from 2.5YR 5/10 to 5YR 8/8.

*Pollen*.—Present. Self-sterile, pollinator required. Color varies from 2.5Y 7/8 to 5Y 7/12.

*Pistil*.—Normally 1. Average length 7.2 mm. Position of stigma an average of 0.7 mm below anthers. Surface-glabrous. Color varies from 10Y 8.5/6 to 2.5GY 8/6.

*Fragrance*.—Moderate.

*Color*.—N 9.5/ (white).

*Number flowers per flower bud*.—Average 3, varies from 1 to 4.

*Pedicel*.—Average length 8.6 mm. Average width 0.6 mm. Color varies from 2.5GY 6/8 to 5Y 6/8. Surface — glabrous.

Fruit:

*Maturity when described*.—Firm ripe.

*Date of first picking*.—Oct. 18, 2012.

*Date of last picking*.—Oct. 25, 2012, varies slightly with climatic conditions.

*Size*.—Large. Average diameter axially 71.9 mm. Average transversely in suture plane 65.5 mm. Average weight 161.9 grams, varies slightly with fertility of the soil, amount of thinning and climatic conditions.

*Form*.—Elongated, heart shape, flattened at base, elongated near apex.

*Suture*.—Nearly smooth, extends from base to apex.

*Ventral surface*.—Nearly smooth.

*Apex*.—Slight tip.

*Base*.—Flat.

*Stem cavity*.—Rounded to slightly elongated in suture plane. Average depth 6.7 mm. Average diameter 3.4 mm.

Stem:

*Size*.—Small to medium. Average length 15.9 mm. Average diameter 3.7 mm.

*Color*.—Varies from 10YR 5/4 to 10YR 4/4.

Flesh:

*Ripens*.—Evenly.

*Texture*.—Firm, meaty.

*Fibers*.—Few, small, tender.

*Firmness*.—Firm, comparable to other commercial varieties.

*Aroma*.—Slight.

*Amydgalin*.—Undetected.

*Eating quality*.—Very good.

*Flavor*.—Very good, good balance between acid and sugar.

*Juice*.—Heavy amount, enhances flavor.

*Brix*.—Average Brix 20.8°, varies slightly with amount of fruit per tree and climatic conditions.

*Color*.—Varies from 10YR 8/8 to 2.5Y 8/6.

*Pit cavity*.—Average length 27.2 mm. Average width 21.3 mm. Average depth 6.7 mm. Color varies from 5YR 6/12 to 10YR 6/6.

Skin:

*Thickness*.—Medium.

*Surface*.—Slightly waffled.

*Bloom*.—Moderate amount.

*Tendency to crack*.—Very slight.

*Color*.—Ground color varies from 5Y 9/2 to 5Y 9/4. Overspread with 5R 2/2 to 7.5R 3/6.

*Tenacity*.—Tenacious to flesh.

*Astringency*.—Undetected.

Stone:

*Type*.—Clingstone.

*Size*.—Medium to large. Average length 26.2 mm. Average width 20.3 mm. Average thickness 11.3 mm.

*Form*.—Ovoid.

*Base*.—Flat.

*Apex*.—Pointed. Average length 1.3 mm.

*Surface*.—Slightly pitted throughout. One shallow groove on each side of suture extending from base to apex. Very small, short ridges running from base to apex approximately ½ distance of stone.

*Sides*.—Unequal, one side extending further outward from suture plane.

*Ridges*.—Small, extending from base to apex.

*Tendency to split*.—None.

*Color*.—Varies from 7.5YR 6/8 to 7.5YR 3/6 when dry.

Kernel:

*Size*.—Medium. Average length 14.2 mm. Average width 10.0 mm. Average depth 4.4 mm.

*Form*.—Ovoid.

*Viability*.—Viable, complete embryo development.

*Skin color*.—Varies from 7.5YR 4/6 to 10YR 5/8.

Use:

*Dessert*.—Market — local and long distance.

Keeping quality: Good, held firm in cold storage at 38° to 42° F. for 2 weeks without internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

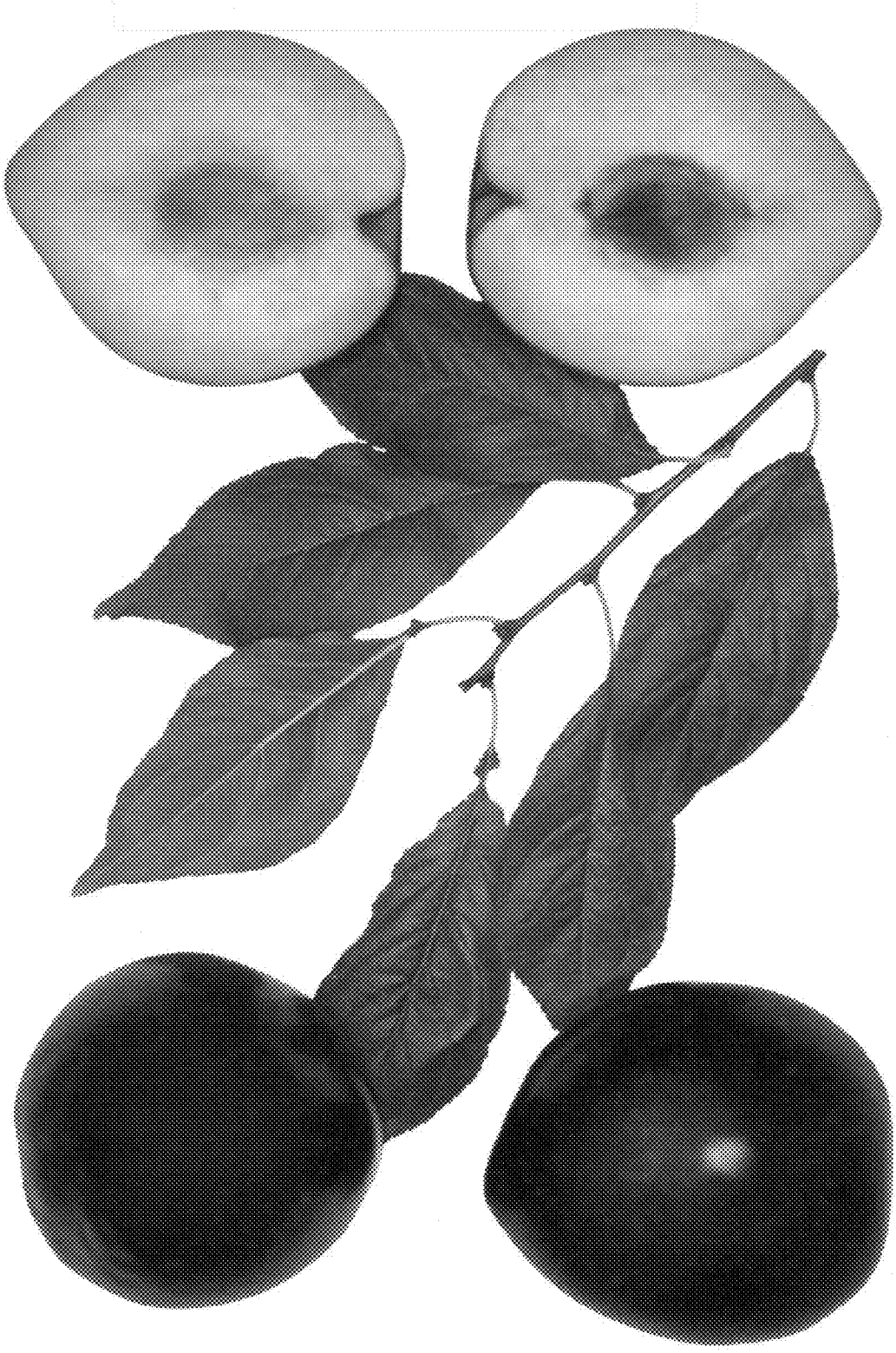

* * * * *